US010251861B2

(12) United States Patent
Sen et al.

(10) Patent No.: US 10,251,861 B2
(45) Date of Patent: Apr. 9, 2019

(54) METHODS FOR TREATING BURN AND SCAR INJURY USING TOCOTRIENOL COMPOSITIONS

(71) Applicant: Ohio State Innovation Foundation, Columbus, OH (US)

(72) Inventors: Chandan Sen, New Albany, OH (US); Sashwati Roy, New Albany, OH (US); Savita Khanna, New Albany, OH (US); Cameron Rink, Galloway, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 70 days.

(21) Appl. No.: 14/406,403

(22) PCT Filed: Jun. 7, 2013

(86) PCT No.: PCT/US2013/044694
§ 371 (c)(1),
(2) Date: Dec. 8, 2014

(87) PCT Pub. No.: WO2013/185024
PCT Pub. Date: Dec. 12, 2013

(65) Prior Publication Data
US 2015/0182493 A1    Jul. 2, 2015

Related U.S. Application Data

(60) Provisional application No. 61/657,443, filed on Jun. 8, 2012.

(51) Int. Cl.
| *A61K 31/353* | (2006.01) |
| *A61K 36/88* | (2006.01) |
| *A61K 36/889* | (2006.01) |
| *A61K 36/899* | (2006.01) |
| *A61K 36/8998* | (2006.01) |

(52) U.S. Cl.
CPC ............ *A61K 31/353* (2013.01); *A61K 36/88* (2013.01); *A61K 36/889* (2013.01); *A61K 36/899* (2013.01); *A61K 36/8998* (2013.01)

(58) Field of Classification Search
CPC .... A61K 31/353; A61K 36/88; A61K 36/889; A61K 36/899; A61K 36/8998
See application file for complete search history.

(56) References Cited

U.S. PATENT DOCUMENTS

| 5,217,992 A | 6/1993 | Wright et al. |
| 5,276,361 A | 1/1994 | Bartlett |
| 5,348,974 A | 9/1994 | Wright et al. |
| 5,376,361 A * | 12/1994 | Perricone ............... A61K 8/498 424/59 |
| 5,591,772 A | 1/1997 | Lane et al. |
| 5,821,264 A | 10/1998 | Lane et al. |
| 5,919,818 A | 7/1999 | Lane et al. |
| 5,965,618 A | 10/1999 | Perricone |
| 6,054,128 A | 4/2000 | Wakat |
| 6,239,171 B1 | 5/2001 | Lane et al. |
| 6,319,942 B1 * | 11/2001 | Perricone ............. A61K 8/0208 514/440 |
| 6,358,997 B1 | 3/2002 | Clark et al. |
| 6,395,757 B1 | 5/2002 | Bobrove et al. |
| 6,439,028 B1 * | 8/2002 | Imhof ................... A61B 5/441 73/24.04 |
| 6,596,306 B1 | 7/2003 | Ho et al. |
| 6,703,384 B2 | 3/2004 | Sanders et al. |
| 6,977,270 B2 | 12/2005 | Baldenius et al. |
| 7,329,688 B2 | 2/2008 | Naguib et al. |
| 2002/0061924 A1 | 5/2002 | Terao et al. |
| 2002/0120001 A1 | 8/2002 | Babish et al. |
| 2002/0172721 A1 | 11/2002 | Boulos et al. |
| 2003/0104078 A1 | 6/2003 | Barrett-Reis et al. |
| 2003/0236301 A1 | 12/2003 | Sanders et al. |
| 2004/0092519 A1 | 5/2004 | Hassan |
| 2004/0102421 A1 | 5/2004 | Ames et al. |
| 2005/0228041 A1 | 10/2005 | Sen et al. |
| 2006/0275228 A1 | 12/2006 | Bissett et al. |
| 2009/0088467 A1 | 4/2009 | Nesaretnam |
| 2010/0047332 A1 | 2/2010 | Lavin |
| 2010/0278784 A1 | 11/2010 | Pojasek et al. |
| 2013/0309202 A1 | 11/2012 | Sen et al. |
| 2014/0024624 A1 | 1/2014 | Sen et al. |

FOREIGN PATENT DOCUMENTS

| WO | 96/19214 A1 | 6/1996 |
| WO | 2000/045815 A1 | 8/2000 |
| WO | 2011/001258 A1 | 1/2011 |
| WO | 2013/173823 A1 | 11/2013 |
| WO | 2013/185022 A1 | 12/2013 |
| WO | 2013/185024 A1 | 12/2013 |
| WO | 2014/014517 A1 | 1/2014 |

OTHER PUBLICATIONS

U.S. National Institutes of Health, "NCT00700791", ClinicalTrials. gov, 2009, pp. 1-3.*
PCT International Preliminary Report on Patentability, PCT/US2013/041794 filed May 20, 2013, dated Nov. 27, 2014.
PCT International Preliminary Report on Patentability, PCT/US2013/044690 filed Jun. 7, 2013, dated Dec. 18, 2014.
PCT International Preliminary Report on Patentability, PCT/US2013/044694 filed Jun. 7, 2013, dated Dec. 18, 2014.
PCT International Search Report and the Written Opinion, PCT/US2013/041794 filed May 20, 2013, dated Oct. 24, 2013.
PCT International Search Report and the Written Opinion, PCT/US2014/047633 filed Jul. 22, 2014, dated Jan. 22, 2015.
PCT International Search Report and the Written Opinion, PCT/US2013/044690 filed Jun. 7, 2013, dated Nov. 8, 2013.

(Continued)

*Primary Examiner* — Sreenivasan Padmanabhan
*Assistant Examiner* — Jody L Karol
(74) *Attorney, Agent, or Firm* — Meunier Carlin & Curfman LLC

(57) ABSTRACT

The present invention provides methods to improve scar and burn outcome utilizing tocotrienols. In particular, various skin pathologies may be treated using the present methods. The present invention also provides methods to increase skin tissue concentrations of tocotrienols.

15 Claims, 6 Drawing Sheets

(56) References Cited

OTHER PUBLICATIONS

PCT International Search Report and the Written Opinion, PCT/US2013/032134 filed Mar. 15, 2013, dated Jun. 10, 2013.
PCT International Search Report and the Written Opinion, PCT/US2013/044694 filed Jun. 7, 2013, dated Nov. 12, 2013.
Asciutti-Moura et al., "Fatty Acid Composition of Serum Lipids and its Relation to Diet in an Elderly Institutionalized Population", The American Journal of Clinical Nutrition, 1988, vol. 48, pp. 980-987.
Bubniak, "Daily Aspirin Ingestion Risks Averted by Natural Alternatives", Daily Aspirin Use Alternatives Eliminate Risks, 2011, Examiner.com, Web Article accessed May 8, 2013, pp. 1-3.
Campbell et al., "Aspirin Dose for the Pervention of Cardiovascular Disease", Journal of the American Medical Association (JAMA), 2007, vol. 297, No. 18, pp. 2018-2024.
McArdle et al., "Effects of Oral Vitamin E and β-carotene Supplementation on Ultraviolet Radiation—Induced Oxidative Stress in Human Skin", The American Journal of Clinical Nutrition, 2004, vol. 80, pp. 1270-1275.
NutraSource, "Generally Recognized as Safe (GRAS) Determination for the Use of Palm Tocotrienal Rich Factions (TRF) as Ingredients in Food", GRAS Notice (GRN) No. 307, 2009, pp. 1-17.
Patel et al., "Oral Tocotrienols Are Transported to Human Tissues and Delay the Progression of the Model for End-Stage Liver Disease Score in Patients", The Journal of Nutrition, 2012, vol. 142, pp. 513-519.
Qureshi et al., "Tocotrienols-induced inhibition of platelet thrombus formation and platelet aggregation in stenosed canine coronary arteries", Lipids in Health and Disease, 2011, vol. 10, No. 58, pp. 1-13.
Rasool et al., "Dose Dependent Elevation of Plasma Tocotrienol Levels and Its Effect on Arterial Compliance, Plasma Total Antioxidant Status, and Lipid Profile in Healthy Humans Supplemented in Tocotrienol Rich Vitamin E", Journal of Nutritional Science a.
Rink et al., "Tocotrienol Vitamin E Protects Against Preclinical Canine Ischemic Stroke by Inducing Arteriogenesis", Journal of Cerebral Bloos Flow & Metabolism, 2011, vol. 31, pp. 2218-2230.
Ziaei et al., "The Effect of Vitamin E on Hot Flashes in Menopausal Women", Gynecologic and Obstetric Investigation, 2007, vol. 64, No. 4, pp. 204-207, Abstract Only.
Affah et al., "Effect of Tocotrienol Rich Fraction (TRF) of Fibroblasts from Normal and Hypertrophic Scar Tissues In Vitro", International Medical Journal, 2009, vol. 16, No. 4, pp. 247-250.
Carotech Inc., "Comparison Between Tocomin Full Spectrum Palm Tocotrienol Complex & Rice Tocotrienol", pp. 1-5, https://web.archive.org/web/20100714160916/http://www.tocotrienol.org/images/stories/pdf_upload/tocomin-rice-new.pdf accessed Jan. 14, 2016.
Carotech BHD, "Tocomin Natural Full Spectrum Palm Tocotrienol/Tocopherol Complex", pp. 1-2, http://wayback.archive.org/web/20100510234107/http://www.carotech.net/index/product_range/tocomin.html accessed Sep. 16, 2014.
Chinese Notification of First Office Action, Application No. CN 201380040076.0, dated Mar. 2, 2016.
European Search Report, Application No. EP 13800955.0, dated Jan. 14, 2016.
Ling, "Tocomin—A novel vitamin E with unique benefits to skin and hair health", Cosmetics, 2009, www.tocotrienol.org/images/stories/pdf_upload/Magazines/tocomin_skin_hair_health_nutracos_aug09.pdf accessed Jan. 14, 2016.
Ling, "Tocomin—A novel vitamin E with unique benefits to skin and hair health", Cosmeceuticals, 2010, www.tocotrienol.org/images/stories/pdf_upload/Magazines/tocomindouble_prolonged_beauty_effectnutracos_may_2010.pdf accessed Jan. 14, 2016.
U.S. National Institutes of Health, "NCT00700791", ClinicalTrials.gov, 2012, pp. 1-4.
U.S. National Institutes of Health, "NCT01579227", ClinicalTrials.gov, 2012, pp. 1-4.
Third Office Action issued in corresponding Chinese Application No. 201380040076.0, dated May 9, 2017, 22 pgs.
Notice of Acceptance issued in corresponding Australian Application No. 2013271442, dated Sep. 22, 2017, 3 pgs.

\* cited by examiner

| Single Site Randomization ||
|---|---|
| Group III: Oral TCT & Topical Placebo | Group IV: Oral TCT & Topical TCT |
| Group I: Oral Placebo & Topical Placebo | Group II: Oral Placebo & Topical TCT |

FIG. 2A

| Bilateral Site Randomization ||
|---|---|
| Group III: Oral TCT & Topical Placebo on the other surgical site | Group IV: Oral TCT & Topical TCT randomized to either left or right surgical site |
| Group I: Oral Placebo & Topical Placebo on the other surgical site | Group II: Oral Placebo & Topical TCT randomized to either left or right surgical site |

FIG. 2B

METHODS FOR TREATING BURN AND SCAR INJURY USING TOCOTRIENOL COMPOSITIONS

CROSS-REFERENCE TO RELATED APPLICATIONS

This application claims the benefit of the PCT/US2013/044694 filed Jun. 7, 2013 which claims priority to U.S. Provisional Patent Application No. 61/657,443 filed Jun. 8, 2012, the entire disclosure of which is expressly incorporated herein by reference.

BACKGROUND OF THE INVENTION

Over 2.4M burn injuries are reported in the United States each year and burns represent one of the most expensive catastrophic injuries to treat. Burn and associated scar injury have both functional and emotional (aesthetic) impact on patients. The current medical standard of care for thermal burn injury targets pain relief (analgesics and NSAIDs) and prevention of infection (topical antibiotics). This invention describes a topical therapeutic intervention that reduces the severity of thermal burn injury as well as burn-induced scar formation. Limiting scar formation has applications for traumatic or surgical induced scar formation as well as scars have both physical (functional) and emotional (aesthetic) impact on patients.

Natural vitamin E exists in two forms: tocopherols and tocotrienols. Both tocopherols and tocotrienols possess a chromanol ring, and within families the isoforms are differentiated as a, $\beta$, $\gamma$, and $\delta$ according to the presence of methyl groups at positions 5, 7, and 8, respectively. Tocopherols are characterized by a saturated side chain, whereas tocotrienols possess an isoprenoid side chain with double bonds at C-3, -7 and -11.

Clinical trials testing the effects of vitamin E in a wide range of major health disorders have come to the general conclusion that vitamin E either is not helpful or could be harmful under certain conditions. Meta-analyses of over 20 randomized, controlled clinical trials testing vitamin E have now reached conclusions that on one hand serve the basis for readjusting public policies and practices while on the other suffer from a major blind spot which is not recognized in any of these reports. While title claims of such meta-analyses address vitamin E as whole, they fail to recognize that the form of vitamin E studied in the vast majority of these trials is $\alpha$-tocopherol which represents one-eighth of the natural vitamin E family.

Palm oil represents a major source of natural tocotrienol. Tocotrienol possess powerful neuroprotective, antioxidant, anti-cancer and cholesterol lowering properties that often differ from the properties of tocopherol. Micromolar amounts of tocotrienol suppress the activity of HMG-CoA reductase, the hepatic enzyme responsible for cholesterol synthesis. Tocotrienols are thought to have more potent antioxidant properties than tocopherol. The unsaturated side chain of tocotrienol allows for more efficient penetration into tissues that have saturated fatty layers such as the brain and liver. Comparative examination of the antioxidant properties of tocopherol and tocotrienol revealed that tocotrienol is advantageous because of their better distribution in the fatty layers of the cell membrane. Recently, an antiangiogenic function of tocotrienol has been reported. Like tocopherol, tocotrienols have been identified to possess distinct functions that may benefit human health, yet tocotrienol accounts for a very small fraction of overall vitamin E research.

Vitamin E: Basic Information

Vitamin E is a fat-soluble vitamin that exists in eight different forms. Each form has its own biological activity, which is the measure of potency or functional use in the body. Vitamin E is a dietary antioxidant that assists in maintaining cell integrity. It is obtained from sunflower, safflower, canola, and olive oils; also from many grains, nuts, fruits as well as fatty parts of meats. The tocotrienol form of natural vitamin E is found in rice and cereals but more abundantly in palm oil. Palm oil is an integral part of daily diet in southeastern Asia.

Only a small amount of vitamin E is needed to meet normal daily requirements. However, research using vitamin E at higher doses than the daily requirement has provided preliminary evidence that it may be helpful for preventing or treating various medical conditions. These uses include treating menstrual pain, cardiac autonomic neuropathy (a complication of diabetes), low sperm count, restless leg syndrome, inflammation of eye tissues, Alzheimer's, Parkinson's and rheumatoid arthritis. Vitamin E also might improve seniors' immune response. Studies show that for people already at high risk for heart disease or with a prior history of the condition, vitamin E may not be helpful. Vitamin E also once was considered a promising treatment for preventing several kinds of cancer. However, current evidence points only to the prevention of prostate cancer.

Natural vitamin E is biologically active. This study involves supplementation of natural vitamin E Synthetic vitamin E (sometimes referred to as dl-alpha-tocopherol) is only half as active as the natural form of vitamin E.

Vitamin E: Safety

To date, there have been no related adverse affects in the inventors' current IRB protocol (200500034). In this protocol, patients are being supplemented 200 mg TCT twice a day for a minimum of 4 weeks prior to surgery. The maximum supplementation has been for over a year (currently on-going supplementation)

Vitamin E 20% cream (tocotrienol cream) has no known toxic effect because the cream is applied topically and systemic absorption is negligible.

Vitamin E is a commonly used, safe nutrient that is required to ensure general health. A recent analysis of data from several clinical trials suggests that excessive vitamin E may raise the risk of death slightly in older individuals with existing medical conditions. Excessive vitamin E may cause bleeding problems resulting in hemorrhaging. The Food and Nutrition Board of the Institute of Medicine has set an upper tolerable intake level (UL) for vitamin E at 1,000 mg (1,500 IU) for any form of supplementary alpha-tocopherol per day. Based, for the most part, on the result of animal studies, the Board decided that because vitamin E can act as an anticoagulant and may increase the risk of bleeding problems, this UL is the highest dose unlikely to result in bleeding problems.

SUMMARY OF THE INVENTION

In a first broad aspect, the inventors have demonstrated that tocotrienol functions as a potent inhibitor of scar lesions caused by thermal (i.e. burn) and mechanical (i.e. surgical) injury. Both oral and topical supplementation of tocotrienol vitamin E attenuates surgical scar or burn formation.

Without being limited by a particular theory, the possible mechanisms of action underlying this new use include, but are not limited to, reducing macrophage infiltration at the injury site, attenuating inflammatory cell proliferation, reducing fibrotic collagen formation, reducing burn denervation, attenuating burn propagation, and increasing vascularization.

Oral (400 mg/day of a tocotrienol-enriched (TE) formulation, Tocovid Suprabio®) and/or topical application of this tocotrienol enriched formulation effectively increased the concentration of tocotrienol in skin cells and may therefore be used independently or combined to deliver tocotrienol to the injury site.

The disclosure describes topical creams and methods of use to effectively reduce the severity of a burn injury and associated scar formation. Commercial applications also encompass methods of treating surgical or trauma-induced scar injury in order to reduce the severity, physical and emotional impact of scar injury.

The present invention provides methods to improve skin scar or burn outcome in a subject with a skin scar or burn pathology, comprising: a.) administering to a subject with skin scar or burn pathology at least one tocotrienol selected from the group consisting of: alpha-tocotrienol; beta-tocotrienol; gamma-tocotrienol; and delta-tocotrienol; and b.) improving skin scar or burn outcome in the subject.

Also provided are methods to slow skin scar or burn progression in a subject with skin scar or burn pathology, comprising: a) administering to a subject with skin scar or burn pathology at least one tocotrienol selected from the group consisting of: alpha-tocotrienol; beta-tocotrienol; gamma-tocotrienol; and delta-tocotrienol; and b.) slowing skin scar or burn progression in the subject.

Also provided are methods to ameliorate the symptoms of skin scar or burn in a subject with end skin scar or burn, comprising: a) administering to a subject with skin scar or burn at least one tocotrienol selected from the group consisting of: alpha-tocotrienol; beta-tocotrienol; gamma-tocotrienol; and delta-tocotrienol; and b.) ameliorating the symptoms of skin scar or burn in the subject.

Also provided are methods for ameliorating the symptoms of skin scar or burn in a subject having a skin scar or burn, comprising: administering a composition consisting essentially of alpha-tocotrienol, gamma-tocotrienol, delta-tocotrienol, and alpha tocopherol to a subject with skin scar or burn, wherein the composition is administered orally and topically, for two to six weeks.

Also provided are methods to increase skin concentration of at least one tocotrienol in a subject, comprising: a) administering to a subject at least one tocotrienol selected from the group consisting of: alpha-tocotrienol; beta-tocotrienol; gamma-tocotrienol; and delta-tocotrienol; and b.) increasing skin concentration of at least one tocotrienol in the subject.

Also provided are such methods, wherein the subject is intolerant of standard therapeutic measures.

Also provided are such methods, wherein the tocotrienol is administered according to Table A.

Also provided are such methods, wherein the tocotrienol is administered according to Table B.

Also provided are such methods, wherein the tocotrienol is administered according to Table C.

A method of any claim herein, wherein the tocotrienol is administered according to Table D.

Also provided are such methods, wherein the tocotrienol is administered according to Table E.

Also provided are such methods, wherein the tocotrienol is administered orally, in a formulation having approximately 15-30% alpha-tocotrienol, approximately 30-50% gamma-tocotrienol, approximately 2-15% delta tocotrienol, and approximately 20-30% alpha tocopherol, by weight of those four ingredients.

Also provided are such methods, wherein the tocotrienol is administered orally, in a formulation having approximately 23% alpha-tocotrienol, approximately 41% gamma-tocotrienol, approximately 9% delta tocotrienol, and approximately 25% alpha tocopherol, by weight of those four ingredients.

Also provided are such methods, wherein the tocotrienol is administered topically, at a concentration of approximately 0.5 ml of 200 mg Tocovid Suprabio® per $cm^2$.

Also provided are such methods, wherein the tocotrienol is administered topically and orally.

Also provided are such methods, which further comprise measuring the tocotrienol concentration in a tissue from the subject, wherein the tissue is selected from the group consisting of: blood; skin; adipose; brain; cardiac muscle; and liver.

Also provided are such methods, wherein tissue concentration of at least one tocotrienol is increased from baseline by a multiplier selected from the group consisting of about: 1.2×; 1.3×; 1.4×; 1.5×; 1.6×; 1.7×; 1.8×; 1.9×; 2×; 3×; 4×; 5×; 6×; 7×; 8×; 9×; 10×; 11×; 12×; 13×; 14×; and 15×.

Also provided are such methods, wherein the tocotrienol composition administered comprises tocopherol, by weight percent total, less than a percent selected from the group consisting of: 50%; 40%; 30%; 20%; 15%; 10%; 5%; and 1%.

Also provided are such methods, wherein the tocotrienol composition is substantially free of tocopherol.

Also provided are such methods, wherein tissue concentration of at least one tocotrienol after administration is selected from the group consisting of about: at least about 0.5 nmol/g to at least about 50 nmol/g; at least about 1 nmol/g to at least about 40 nmol/g; at least about 2 nmol/g to at least about 30 nmol/g; at least about 3 nmol/g to at least about 25 nmol/g; at least about 4 nmol/g to at least about 20 nmol/g; and at least about 5 nmol/g to at least about 15 nmol/g.

Also provided are such methods, wherein the tocotrienol composition is derived from at least one plant selected from the group consisting of: wheat; rice; barley; and palm.

Also provided are such methods, wherein the tocotrienol composition is derived from palm oil.

Also provided are such methods, wherein the tocotrienol composition is Tocovid SupraBio®.

Also provided are methods to treat skin scar or burn in a patient with skin scar or burn, comprising: a) administering at least one daily dose of tocotrienol composition to a patient with skin scar or burn, wherein the tocotrienol composition comprises approximately 123 mg d-alpha tocotrienol; approximately 16 mg d-beta trocotrienol; approximately 225 mg d-gamma tocotrienol; and approximately 51 mg d-delta tocotrienol; and b.) treating scar or burn in the patient.

Also provided are such methods, wherein the scar is a result of a cause selected from the group consisting of: scrape; cut; laceration; surgery; abrasion; and acne.

Also provided are such methods, wherein the scar type is selected from the group consisting of: hypertrophic; keloid; atrophic; and stretch.

Also provided are such methods, which further comprises administering alpha-tocopherol.

Also provided are such methods, which further comprises administering approximately 134.36 mg alpha tocopherol per day.

Also provided are such methods, wherein administration is daily for 4 weeks, after meals.

Also provided are such methods, wherein scar and burn symptom amelioration is measured by a means selected from the group consisting of: Vancouver scar assessment; transepidermal water loss (TEWL); and surface electrical capacitance (SEC).

Various objects and advantages of this invention will become apparent to those skilled in the art from the following detailed description of the preferred embodiment, when read in light of the accompanying drawings.

BRIEF DESCRIPTION OF THE DRAWINGS

FIG. 2A-FIG. 2B. describes the study protocol.

DETAILED DESCRIPTION OF THE INVENTION

Figure 1A:
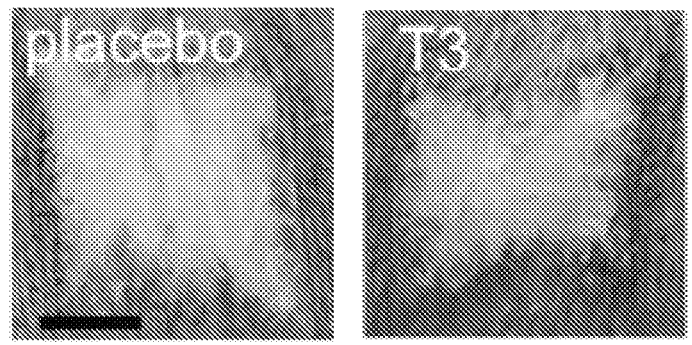
FIG. 1A-FIG. 1D. Topical vitamin E alpha-tocotrienol improves scar outcome. Alpha-tocotrienol content and scar outcomes were assessed in skin 65 days after burn injury. Representative placebo and T3-treated burn scars depicted (A) (scale bar=1 cm). Topical tocotrienol treatment significantly increased alpha-tocotrienol content in scar tissue (B). Color (C) and contour (D) were judged by blinded reviewers according to their respective 5-point scales. Topical tocotrienol significantly improved both color and contour in burn-induced scar. Data are mean+SD (n=8); *p<0.05.
Figure 1B:
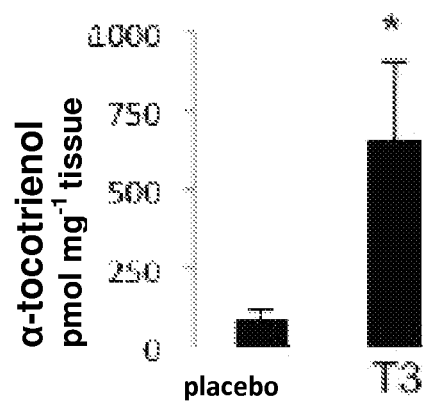
Figure 1C:
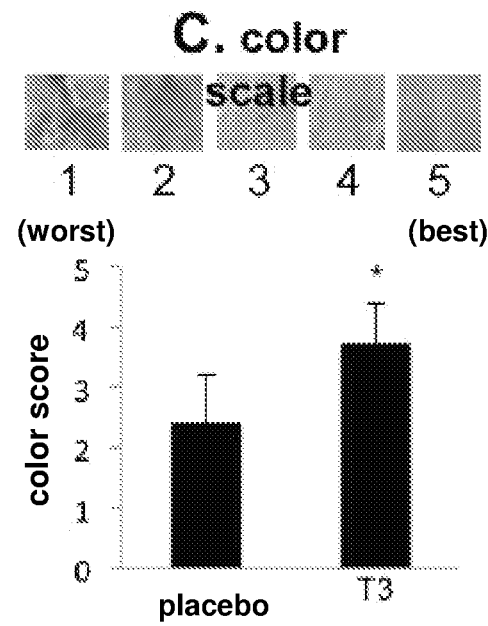
Figure 1D:
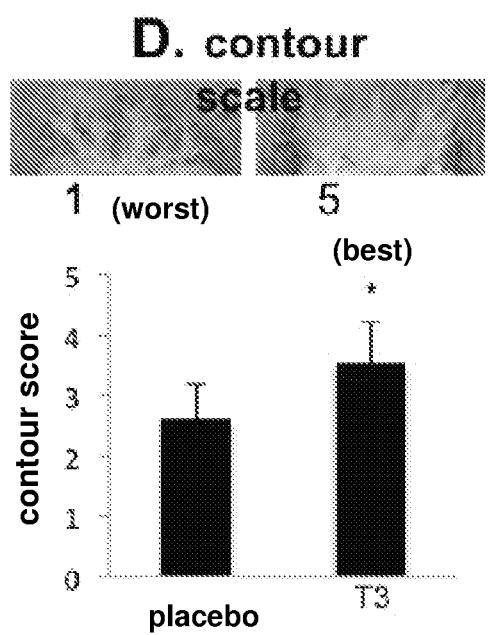
Figure 3A:
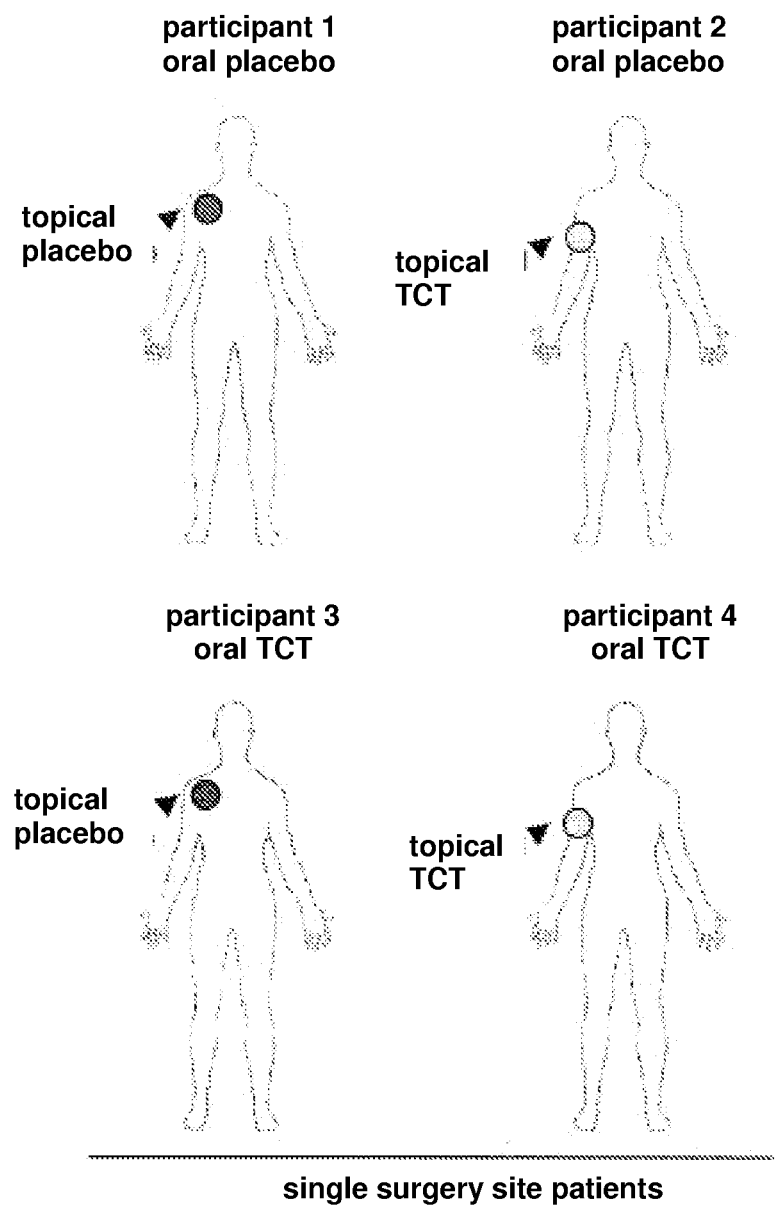
FIG. 3A-FIG. 3B. describes the study protocol.
Figure 3B:
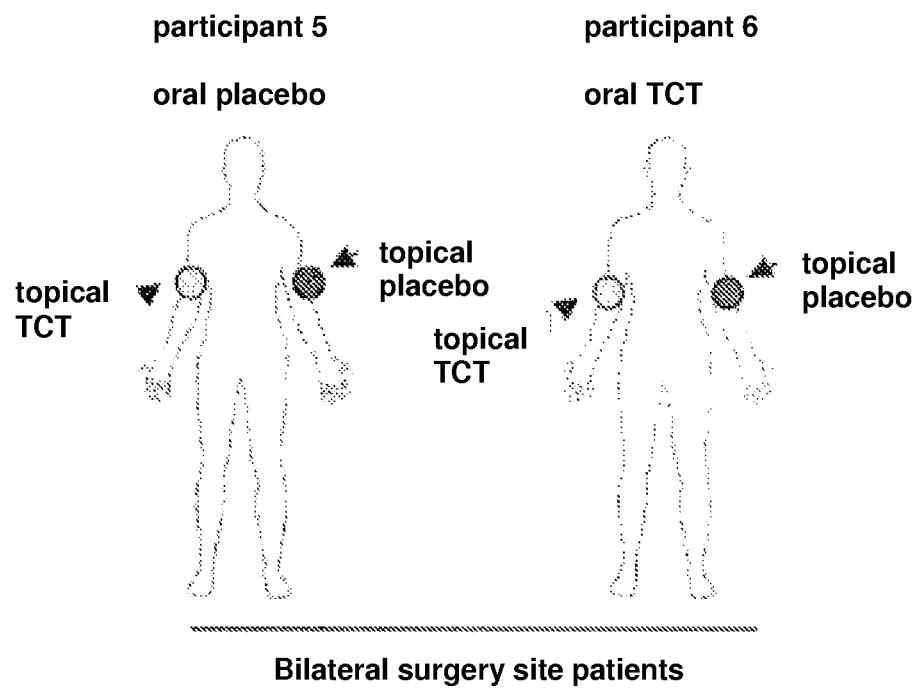
Figure 4:
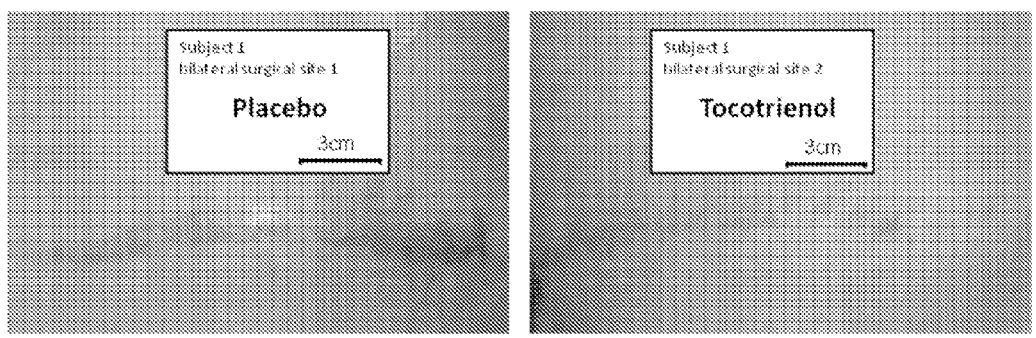
FIG. 4. Bilateral surgical scars from the same subject were treated topically with placebo (vehicle control) or tocotrienol cream for 12 weeks post-operatively as described in Example 2 and then imaged. After 12 weeks, the tocotrienol treated scar (right image) appears less hypertrophic with improved coloration and contour as compared to the placebo treated scar (left image).

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The present invention provides methods to improve skin burn or scar outcome in a subject with a skin burn or scar pathology, comprising: a) administering to a subject with skin burn or scar pathology at least one tocotrienol selected from the group consisting of: alpha-tocotrienol; beta-tocotrienol; gamma-tocotrienol; and delta-tocotrienol; and b.) improving skin burn or scar outcome in the subject. The tocotrienol may be administered according to the following Tables A-E, and as described in the Examples.

TABLE A

Tocotrienol daily dose, by milligrams

| Tocotrienol | Range 1 | Range 2 | Range 3 | Range 4 |
|---|---|---|---|---|
| alpha | 100-150 | 110-140 | 115-130 | 120-125 |
| gamma | 180-270 | 190-260 | 200-250 | 220-230 |
| delta | 35-70 | 40-65 | 45-60 | 48-54 |

TABLE B

Tocotrienol w/w percent, by total tocotrienols

| Tocotrienol | Range 1 | Range 2 | Range 3 | Range 4 |
|---|---|---|---|---|
| alpha | 0-50 | 20-40 | 25-35 | 28-32 |
| gamma | 0-70 | 45-65 | 50-60 | 54-58 |
| delta | 0-25 | 5-20 | 8-15 | 10-14 |

TABLE C

Tocotrienol, by doses per day

| Tocotrienol | Range 1 | Range 2 | Range 3 | Range 4 |
|---|---|---|---|---|
| alpha | 0-6 | 1-5 | 2-4 | 1-2 |
| gamma | 0-6 | 1-5 | 2-4 | 1-2 |
| delta | 0-6 | 1-5 | 2-4 | 1-2 |

TABLE D

Tocotrienol doses, by number of days per week

| Tocotrienol | Range 1 | Range 2 | Range 3 | Range 4 |
|---|---|---|---|---|
| alpha | 0-7 | 1-6 | 2-5 | 6-7 |
| gamma | 0-7 | 1-6 | 2-5 | 6-7 |
| delta | 0-7 | 1-6 | 2-5 | 6-7 |

TABLE E

Tocotrienol doses, by number of weeks per year

| Tocotrienol | Range 1 | Range 2 | Range 3 | Range 4 |
|---|---|---|---|---|
| alpha | .5-52 | 1-20 | 4-20 | 4-12 |
| gamma | .5-52 | 1-20 | 4-20 | 4-12 |
| delta | .5-52 | 1-20 | 4-20 | 4-12 |

The inventors have also observed that oral supplementation in animals results in enhancement of tocotrienol in tissues such as skin, brain, lung etc. Levels of tocotrienol in human tissues following supplementation is currently being investigated by the inventors' laboratory (IRB protocol 200500034). The patients in the inventors' ongoing study are being orally supplemented with 200 mg twice a day. Recently, pharmacokinetic studies have been performed where humans have been orally supplemented with tocotrienol (dose: 692 mg). Based on this work and the inventors' current study, the inventors plan to use (200×2=400 mg/day; note that for alpha-tocopherol 1 mg=1.51 U) for the inventors' study.

Scar formation is the physiological and inevitable end point of mammalian wound healing and there is substantial evidence that inflammation is an essential prerequisite for scarring. Although scar tissue restores the normal skin barrier, the new tissue is inferior in structural, aesthetic, and functional respects. The mammalian wound healing response may have originated during the time of high susceptibility to infection. Therefore, the inventors may have developed speed optimized wound healing where a multiple redundant compensating rapid inflammatory response allows the wound to heal quickly without infection. The scar is then the price mammalians have to pay for evolutionary survival after wounding.

There is a great deal of variation of the quality and size of scars between species and even among various body parts and organs. Human pathological conditions and genetic disorders can lead to excessive scarring such as hypertrophic and keloid scars. Even though the underling mechanisms of scarring have yet to be fully understood, there is an extensive amount of experimental and clinical evidence that points to altered inflammatory and/or cytokine profiles leading to differences in scarring. There are many situations that provide clear evidence that the inflammatory response during wound healing is closely linked to scar formation. A classic example is the scarless healing of early fetal skin. There are many differences between the fetus and the adult, but the hallmark of fetal skin is the lack of typical inflammatory response. Scarless fetal wounds heal with a lack of inflammation, and the onset of scarring during fetal wound healing corresponds with the presence of an acute inflammatory response. The importance of inflammation in scar formation is highlighted by the fact that introduction of inflammation into normally scarless-healing wounds results in increases in wound macrophages, neutrophils, collagen deposition, and scarring.

Proinflammatory cytokines, such as IL-1a, IL-1β, IL-6, and TNF-a, have been shown to be pivotal mediators during different cutaneous inflammatory processes. Proinflammatory cytokines are strongly upregulated during the inflammatory phase of healing; and several cell types, including polymorphonuclear neutrophils, monocytes, and macrophages, amplify the inflammatory response though TNF-a, IL-1β, and IL-6. Interleukins (ILs) regulate the chemotaxis and activation of inflammatory cells. IL-6 stimulates monocyte chemotaxis and macrophage activation, while IL-8 attracts neutrophils and stimulates neovascularization. Wounding stimulates a rapid increase in IL-6 and IL-8, which persists in the adult, but disappears quickly in the fetus. Platelet derived growth factor (PDGF) induces adult fibroblast production of IL-6. In turn, the addition of IL-6 to fetal wounds produces early scarring. In fetal, compared to adult fibroblasts, IL-6 and IL-8 expression are lower at baseline and after stimulation with (PDGF). IL-10, an anti-inflammatory cytokine, functions by decreasing production of IL-6 and IL-8. In an initial report, adult mouse wounds treated with IL-10 overexpressing adenoviral vector exhibited reduced inflammation and scarless healing.

Nuclear factor kB (NF-kB) is a transcriptional regulator that plays a central part in responses to inflammatory signaling not only through Toll-like receptors, but also through TNF receptors and the IL-1 receptor. Among the molecules induced by NF-kB are cytokines, chemokines, effector molecules of immunity, pro-survival factors, and adhesion molecules.

Both transforming growth factor (TGF) isoforms have pro-fibrotic functions and promote scar formation. In wound tissue, TGF is released by macrophages. Their expression is increased in normal wound healing, and exogenous administration of this growth factor to adult wounds increases collagen, proteoglycan, and inflammatory cell accumulation. Moreover, treatment of adult rat wounds with neutralizing antibody to TGF isoforms reduces scar formation.

Excess inflammation is associated with impaired wound healing. Wound disorders in the clinic present as hypertrophic scars or as non-healing chronic wounds. Despite the different types of association with chronic wounds (i.e. diabetes mellitus, pressure necrosis, and vasculitis) most non-healing wounds fail to progress though the normal phases of wound repair, and instead remain in a chronic inflammatory state. Hypertrophic scars represent an exaggerated proliferative response to wound healing that stays within the boundaries of the original wound. Keloids, in contrast, have a more aggressive life cycle and extend beyond the original borders. It is estimated that keloids occur in about 10% of people. While most people never form keloids, others develop them after minor injuries, such as insect bites or pimples. Darkly pigmented people seem to be more prone to forming keloids, but men and women are equally affected. Keloids are considered a benign tumor, but they are mainly a cosmetic nuisance and never become malignant. Theories for the causes of keloid scarring include a deficiency or an excess in melanocyte hormone (MSH), decreases in the percentage of mature collagen and an increase in the percentage of soluble collagen. A hypertrophic scar looks similar to a keloid scar; however, hypertrophic scars are more common, are not as large as keloids, and may fade with time. Keloid and hypertrophic scars develop most frequently in wounds with high skin tension and especially on the upper truncus.

In contrast to extensive studies on tocopherol, very little is known about tocotrienol. A recent study has shown that gamma-tocotrienol completely abolished tumor necrosis factor a (TNF-a)-induced NF-KB activation, while a similar dose of gamma-tocopherol had no effect. Besides TNF, gamma-tocotrienol also abolished NF-KB activation induced by phorbol myristate acetate, okadaic acid, lipopolysaccharide, cigarette smoke, IL-1I, and epidermal growth factor. Constitutive NF-KB activation expressed by certain tumor cells were also nullified by y-tocotrienol. gamma-Tocotrienol was shown to inhibit IKBa degradation by inhibiting TNF-induced activation of IKBa kinase (IKK). Therefore, gamma-tocotrienol inhibits NF-KB activation through inhibition of IKK. gamma-tocotrienol was also shown to inhibit TNF-induced phosphorylation of p65 and TNF induced Akt activation. gamma-tocotrienol has been shown to inhibit TAK 1/TAB 1-induced NF-KB dependant reporter gene expression. TKA1, a member of the MAPK kinase kinase, was originally identified as a key regulator of MAPK activation in TGF-induced signaling pathways. It is activated by various inflammatory stimuli, including TNF, IL-1, and LPS. COX2, cyclin D1, VEGF, ICAM-1, MMP-9 and c-Myc have NFkB binding sites in their promoters and inhibition of NF-KB activation of y-tocotrienol suppresses the production of these proteins. Finally, the inhibition of NF-KB activation by gamma-tocotrienol was shown to be not cell type specific. Instead, it was shown to have an effect in myeloid, human epithelial, and MCF-7 cells.

Recently, a palm tocotrienol mixture was able to prevent the increase of IL-1 and IL-6 in serum due to nicotine treatment; whereas tocopherols were not. Serum levels of IL-6 in tocotrienol treated rats were significantly lower than even before nicotine and tocotrienol treatment. Also, tocotrienol has previously been shown as the most effective form of vitamin E for reducing endothelial expression of adhesion molecules (ICAM, VCAM, and E-selectin) and adhesion to monocytes.

Currently, there is no single optimal modality that can eliminate or prevent normal, hypertrophic, or keloid scarring. The most accepted treatment for old and new hypertrophic scars is silicone gel sheeting. Silicone ointment or gel alone, however, is less effective than silicone sheeting. Pressure therapy has demonstrated some efficacy, but is cumbersome to use and is not standardized. Problems associated with pressure therapy are limited by use on areas other than the face and high-motion. Anatomic depression, low patient compliance, and side effects of local skin maceration are significant problems with such treatment. Mederma® is an onion extract cream sold over-the-counter in the U.S. for the treatment of scars. It is currently the number one recommended treatment for scar by doctors and pharmacists. However, products in the United States containing onion extract do not improve scar cosmesis or symptomatology when compared with petrolatum-based ointment. Prescription Imiquimod 5% cream has been shown to improve the quality of new hypertrophic scars after surgery in a preliminary clinical trial, but further studies are necessary. Imiquimod 5% cream, a topical immune response modifier, is approved for treatment of genital warts, basal cell carcinoma, and actinic keratoses. Imiquimod stimulates proinflammatory cytokines, especially interferon-a, which increases collagen breakdown [30].

Tocotrienol may be an effective tool to prevent or reduce normal, hypertrophic, or keloid scarring by mediating the inflammatory response. Tocotrienol is a safe and convenient treatment that could be used by mouth or topically. There has never been a study on the effectiveness of tocotrienol in preventing or reducing scar formation. The inventors' observations from an 'ongoing IRB protocol led the inventors to evaluate the potential of tocotrienol in such respect.

The natural vitamin E family is composed of eight members, equally divided into two classes; tocopherols (TCP) and tocotrienols (TE). TCP are characterized by a saturated phytyl side chain with three chiral carbons whereas TE possess a farnesyl side chain with double bonds at carbons 3, 7, and 11. Within each class, isomers are differentiated by $\alpha$, $\beta$, $\gamma$, and $\delta$ according to the position and degree of methylation on the chromanol head. TCP represent the primary form of vitamin E in green leafy vegetables, while TE are found in highest concentration in seeds of monocotyledons that include the wheat, rice, barley, and palm.

It is important to note that in all of the studies based on which vitamin E has been claimed to have potential harmful effects, the a-tocopherol, not a-tocotrienol, form of vitamin E was investigated. The eight natural isoforms of vitamin E are known to possess unique biological functions. For example, a-tocopherol and a-tocotrienol have functions that are unique to each other. Thus, concerns related to a-tocopherol may not be directly applicable to a-tocotrienol. The vast majority (>98%) of the current literature on vitamin E addresses a-tocopherol. As the inventors learn more about the unique functions of the other forms of vitamin E and about the potential safety issues of a-tocopherol, interest in non-a-tocopherol forms of vitamin E is rapidly rising.

Functions of Ingredients

Methyl paraben and propyl paraben—functions as preservatives. The Cosmetic Ingredient Review (CIR) reviewed the safety of methylparaben, propylparaben, and butylparaben in 1984 and concluded they were safe for use in cosmetic products at levels up to 25%. In December 2005, the CIR Panel again determined that there was no need to change its original conclusion that parabens are safe as used in cosmetics. They are included in the FDA Inactive Ingredients Guide for topical preparations. It is also accepted for use as a food additive in Europe and affirmed GRAS Direct Food Substances in USA at levels up to 0.1% (Handbook of Pharmaceutical Excipients, 4th Edition, 2003, published by the Pharmaceutical Press and the American Pharmaceutical Association).

Carbomer—gelling agent for the aqueous phase. Included in the FDA Inactive Ingredients Guide (oral suspension and tablets, ophthalmic, rectal and topical preparations). It is used extensively in nonparenteral products, particularly topical liquid and semisolid preparations. Carbomer is generally regarded as essentially nontoxic and nonirritant material; there is no evidence in humans of hypersensitivity reactions to carbomer used topically (Handbook of Pharmaceutical Excipients, 4th Edition, 2003, published by the Pharmaceutical Press and the American Pharmaceutical Association).

Glycerin—also referred to as glycerol. This functions as a humectant. Glycerin is listed as GRAS and accepted as food additives. It is included in the FDA Inactive Ingredients Guide for topical preparations.

Triethanolamine—an alkalizing agent to neutralize the carbomer to build up the gel structure as well as an emulsifying agent. Also referred to as Trolamine in USPNF. Included in the FDA Inactive Ingredients Guide (rectal, topical and vaginal preparations).

Polyoxyl 40 castor oil—an emulsifying agent. Included in the FDA Inactive Ingredients Guide (IV injections and ophthalmic solutions).

Cetomacrogol emulsifying wax—also referred to nonionic emulsifying wax. It is used as an emulsifying agent and stiffening agent. Cetomacrogol emulsifying wax is included in the FDA inactive ingredient guides (topical aerosols, emulsions, lotions and ointments). It is generally regarded as essentially nontoxic and nonirritant material.

Cetyl alcohol—an emulsifying agent and stiffening agent. Included in the FDA Inactive Ingredient Guides (creams, emulsions and topical aerosols).

Stearic acid is a stiffening agent. It is listed as GRAS and accepted as a food additive in Europe (fatty acids). Included in the FDA Inactive Ingredient Guides (topical and vaginal preparations)

Propylene Glycol Caprylate is an emulsifying agent.

Dry Flo AF—hydrophobically modified corn starches which is used for its ability to enhance the aesthetics of a skin care products and mitigate greasiness in the cream formulation. It is manufactured by National Starch and Chemical Company, New Jersey, USA.

EXAMPLES

Example 1. Following 12 wk of TE Supplementation, Skin Concentration of $\alpha$TE, $\gamma$TE, and $\delta$TE was Significantly Elevated. Combined Data for Males and Females Showed a Significant Increase in all Three Isoforms at 12 wk. Oral TE Supplementation had No Significant Effect on $\alpha$TCP or $\gamma$TCP Skin Concentration Human Participants The study protocol was reviewed and approved by the institutional review board of The Ohio State University. All patients provided written informed consent. Due to limitations in obtaining healthy adult human tissue, whole blood and skin biopsy samples were taken from the Healthy Participants Group while vital organ tissue was acquired from the Surgical Patients Group.

Healthy Participants Group

Whole blood and skin vitamin E concentration were compared at baseline (pre-supplementation) to samples collected after 12 wk of supplementation with TE. Healthy participants (n=16) received 400 mg of TE daily. Adult volunteers provided two skin biopsy and three blood samples. Skin biopsies were collected from the right ($1^{st}$ biopsy at 0 wk) and left ($2^{nd}$ biopsy at 12 wk) inner thigh. Whole blood was taken at 0, 6 and 12 wk. Healthy participants were chosen for this study because they could be supplemented for a defined time period (not bound by scheduled surgery as in the Surgical Patients Group). This allowed the inventors to collect pre-supplementation baseline samples. In this group participants were not supplemented with TCP as each participant was naive to TE and acted as their own control. Inclusion criteria for the Healthy Participants Group included: age 21-40 years old, good health, non-smoker, non-pregnant or non-breastfeeding, and no recent (past 6 mo) or current use of supplements containing vitamin E. Exclusion criteria for the Healthy Participants Group included: diabetes or HIV infection, receiving immunosuppression therapy, neurological disease, and alcohol or drug use.

Surgical Patients Group

Adult surgical patients were randomized to supplementation of either 400 mg TCP or 400 mg TE daily. Exclusion criteria included current or recent dietary supplementation of vitamin E and surgical patients under 21 y of age. Both TCP and TE supplemented groups received comparable physician prescribed diets which did not include additional dietary supplements.

Supplementation Regimen and Compliance

For the current study, vitamin E capsules were supplied by Carotech Inc., 21 Balmoral Court, Talmadge Village, Edison, N.J. 08817, USA. The entire study was conducted using vitamin E gel capsules manufactured in a single batch and immediately shipped to the inventors. Capsule content was validated using a sensitive coulometric electrode detection method developed by the inventors' laboratory.

The Surgical Patients Group participants were randomized to receive either 400 mg TE (200 mg Tocovid SupraBio b.i.d.) or 400 mg TCP (200 mg b.i.d.). The Healthy Participants Group received only 400 mg TE (200 mg b.i.d.). A single 200 mg Tocovid SupraBio softgel capsule contains 61.52 mg d-alpha-tocotrienol, 8.11 mg d-beta-tocotrienol; 112.8 mg d-gamma-tocotrienol, and 25.68 mg d-delta-tocotrienol. TCP gel capsules contained 200 mg of d-alpha-tocopherol. Vitamin E gel capsules were sealed in blister packs. To determine compliance, study participants mailed empty packages back to the clinic every two weeks. Participant supplementation compliance for the study was >90%.

Supplementation length for surgical groups was determined by the initiation of vitamin E supplementation to the day before scheduled surgery. For all surgical patients, a minimum of 4 wk of supplementation was desired. However, in some cases physician-directed necessity of surgery did not permit a full 4 wk. Tissue specific mean, minimum, and maximum length of supplementation for patients is reported in Supplemental Table 1.

SUPPLEMENTAL TABLE 1

| Length of vitamin E supplementation[1] | | |
|---|---|---|
| Organ | n[2] | days |
| Blood | | |
| TCP | 16 | 84 ± 0 (84-84) |
| TE | 16 | 84 ± 0 (84-84) |
| Skin | | |
| TCP | 16 | 84 ± 0 (84-84) |
| TE | 16 | 84 ± 0 (84-84) |
| Adipose | | |
| TCP | 4 | 83 ± 55 (14-145) |
| TE | 5 | 157 ± 75 (88-280) |
| Brain | | |
| TCP | 4 | NA[3] |
| TE | 4 | 261 ± 278 (78-672) |

SUPPLEMENTAL TABLE 1-continued

| Length of vitamin E supplementation[1] | | |
|---|---|---|
| Organ | n[2] | days |
| Heart | | |
| TCP | 3 | 14 ± 5 (9-18) |
| TE | 5 | 155 ± 167 (30-443) |
| Liver | | |
| TCP | 3 | 144 ± 16 (129-161) |
| TE | 4 | 181 ± 129 (8-309) |

[1]Values are mean ± SD (range)
[2]For adipose, brain, heart, and liver n represents patients that went to surgery, not total enrollment
[3]Autopsy tissue used-no supplementation Vitamin E Extraction and Analyses Excised tissues were minced, rinsed in phosphate buffered saline to remove blood, and stored in liquid nitrogen until analysis. Vitamin E extraction was performed using a highly sensitive HPLC-coulometric electrode array detector (CoulArray Detector Model 5600 with 12 channels; ESA Inc., Chelmsford, Mass., USA).

Example 2. Observations from the Inventors' Ongoing Study Indicates that Pre-Treatment with TCT Improves the Appearance of Scars The overall goal of this randomized double-blind study is to determine the efficacy of tocotrienol (TCT), a natural form of vitamin E, in preventing or reducing scar formation in human skin wounds.

Specific Objectives:

1. To determine the efficacy of TCT in improving the appearance of post-surgical scars following oral supplementation (200 mg×2 per day for a minimum of 4 weeks prior to surgery and 12 weeks post surgery).

2. To determine the efficacy of TCT in improving the appearance of post-surgical scars following topical application for 12 weeks.

3. To establish a cause and effect relationship between TCT intake and scar performance, compliance will be monitored by measuring the level of TCT in serum, skin tissue, and adipose tissue.

Patients undergoing single site and bilateral site body contouring surgical procedures will be recruited from The Division of Plastic Surgery at The Ohio State University Medical Center.

Oral Supplementation

Patients undergoing either single site or bilateral site surgery will start oral placebo (vehicle only), or oral TCT supplementation for a minimum of 4 weeks before surgery to 12 weeks post surgery (objective 1). Patients undergoing surgery will be recruited a minimum of 4 weeks prior to surgery.

Topical Supplementation

Patients undergoing bilateral site surgery will be given both topical TCT cream (20%) and vehicle only cream (placebo). Patients will topically apply the TCT cream to the surgical site on one side of their body. To the other surgical site, they will apply the vehicle only cream (objective 2). Patients undergoing single site surgery will be randomized to either topical TCT cream (20%) or vehicle only cream (placebo). The patient will topically apply the cream (either TCT or placebo) at the surgical site on their body Randomization Single site surgery patients will be randomized to one of 4 treatment groups defined by the 2 by 2 combination of oral TCT/oral placebo vs. topical TCT/topical placebo. See the single site randomization diagram below. Patients undergoing bilateral site surgery will be randomized to either oral TCT or oral placebo followed by either TCT cream on their right or left surgical site. Placebo cream will be applied to the opposite site. See the bilateral site randomization diagram below. Bilateral site surgery subjects will be their own treatment and control for the topical administration and a single patient will be in both groups I and II or in groups III and IV.

Patients will enter the study either as single site subjects or as bilateral site subjects. The single site subjects will be randomized into the four groups defined by oral (TCT or placebo) and topical (TCT or placebo). Each single site subject will counted once towards the 42 subjects per group required for this study. Bilateral site subjects will be randomized into one of four groups defined by oral TCT plus topical TCT on the right surgical site, oral TCT plus topical TCT on the left surgical site, oral placebo plus topical TCT on the right surgical site, or oral placebo plus topical TCT on the left surgical site. Topical placebo will be applied to the other surgical site in the bilateral site subjects and these subjects will counted twice towards the 42 subjects pre group as they have both topical TCT and topical placebo. Thus if all of the subjects in the study were single site subjects, then a total of 168 subjects would be need to complete this study. If in the other extreme all of the subjects in the study were bilateral site subjects, then a total of 84 subjects would be needed. The actual distribution of single and bilateral site subjects is not known at this time, but whatever the combination is, there will be a total of 168 wound sites from somewhere between 84 and 168 individual subjects in this study. There will be two randomization lists, one for the single surgical subjects and one for the bilateral surgical subjects.

The study will be double blinded. Neither patients nor researchers will know which participants will receive oral placebo or oral TCT treatment. The only identifying objects on the capsules will be the color coding of the blister packs. The creams will also have different color coded labels: one for vehicle only cream and one for cream containing TCT. The decoding information will be held by a consulting statistician at The Center for Biostatistics. An example of a possible participant treatment scenario is shown in the figures.

Product and Dosage Used in this Study 100 mg capsules containing tocotrienol and vehicle only capsules will be provided by Carotech Inc, New Jersey. Tocotrienol is sold over the counter for general human consumption. Tocotrienol (20% TCT) and placebo cream will also be provided by Carotech Inc. A tocotrienol cream is available for human use in Asia.

Source of Vitamin E:

During the last six years, the inventors' laboratory has performed several experimental studies on vitamin E addressing specific isoforms of vitamin E. All of these studies have been performed with vitamin E from one source (Carotech Inc., N.J.) to avoid variations. For the proposed study, vitamin E capsules have been provided by Carotech Inc. The inventors' laboratory specializes in analytical approaches for the assessment of vitamin E. Using a sensitive CouloArray approach, the inventors have analyzed the capsule content to ensure that the study is not affected by variability in vitamin E content. The entire study will be conducted using vitamin E capsules that have been manufactured in one batch and have been recently sent to the inventors.

The dose for TCT pills is based on the equivalent dose range for alpha tocopherol whereby 100 i.u. of alpha tocopherol is equivalent to 91 mg of alpha tocopherol. For the cream, the dose is based on commercially available tocopherol preparation in Malaysia such as Natopherol Dermal Night from Abbot Malaysia which contains 40 i.u. of alpha tocopherol (equivalent to 36.4 mg of alpha-tocopherol per application). The amount of tocotrienol applied by the volunteers using the TCT cream is approximately similar to the above.

Prevention of air exposure at the wound site is mainly due to occlusive effect of a topical preparation, especially ointments. In this case, a cream is used and prevention of air exposure is therefore less. Many surgeons treat surgical incisions with Neosporin ointment routinely in clinical practice. The vitamin E cream is less occlusive than any ointment.

The oral formulation of tocotrienol will be made available to volunteers in the form of soft gelatin capsules. The tocotrienol soft gelatin capsule is available commercially in Malaysia as Tocovid° Suprabio® 50 mg, Tocovid° Suprabio" 100 mg and Tocovid® Suprabio® 200 mg. These preparations are manufactured under cGMP conditions.

Each Tocovid® Suprabio a 200 mg capsule contains:

| | |
|---|---|
| Tocomin ® 50 | 594.6 mg |
| Soya Oil | 305.4 mg |
| Labrasol ® | 50.00 mg |
| Cremophor EL) | 50.00 mg |

Tocomin® 50 contains a minimum of 50% vitamin E whereby approximately 10% is alpha-tocopherol, 12% of alpha-tocotrienols, 20.6% of gamma-tocotrienols, 1.5% of beta-tocotrienols and 5% of delta-tocotrienols. Tocomin® 50 is produced by Carotech Bhd, Malaysia.

Soya Oil is soybean oil, which is widely used oil and is commonly called 'vegetable oil'. Soybean oil is also used by the food industry in a variety of food products including salad dressings, sandwich spreads, margarine, bread, mayonnaise, non-dairy coffee creamers and snack foods. The high smoke point of soybean oil allows it to be used as frying oil. Soyabean oil is used as a carrier and bulking agent in the formulation.

Labrasol® is a product from Gattefosse SAS, France. It is a mixture of caprylocaproyl polyoxyglycerides and caprylocapryol macrogolglycerides. Labrasol functions as a liquid solubilizer to produce a self emulsifying system. It is monographed in USP/NF latest edition under the monograph's title caprylocaproyl polyoxyglycerides and in the European pharmacopeia under the monograph's title caprylocaproyl macrogolglycerides. A pharmaceutical and nutritional regulatory statement from the supplier, Gattefosse, is as attached.

Cremophor EL® is a product from BASF, Germany. Functions as an emulsifying agent and solubilising agent. Its nonproprietary name is polyoxyl 35 castor oil as listed in USP/NF. It is widely used in oral, topical and parenteral pharmaceutical formulations as well as in cosmetics and animal feed. It is listed in the FDA Inactive Ingredients Guide (IV injections and ophthalmic solutions) and also include in parenteral medicines licensed in UK (Handbook of Pharmaceutical Excipients, 4th Edition, 2003, published by the Pharmaceutical Press and the American Pharmaceutical Association).

A similar cream of 1% concentration is available and being marketed by Hovid Bhd, Malaysia. However, at the low concentration, it is not intended for wound application. For the wound healing study, the cream was specially formulated with a strength of 15%. Below is the formula for the cream. Please note that all ingredients used are approved with reference to USP-NF or are listed in the Cosmetic Ingredient Review (CIR) as "Safe in the present practice and concentrations as described in the safety assessment" or "Safe with qualification" except for Dry Flo AF. The product will be prepared under cGMP conditions.

| Formula | |
| --- | --- |
| Methyl paraben | 0.1% |
| Propyl paraben | 0.01% |
| Carbomer | 0.3% |
| Glycerin | 4.0% |
| Triethanolaime | 0.6% |
| Polyoxyl 40 Castor Oil | 1-5% |
| Cetomacrogol emulsifying wax | 5% |
| Cetyl alcohol | 1.5% |
| Stearic acid | 1.5% |
| Tocomin ® 50C | 30% (containing 15% tocotrienols) |
| Propylene Glycol Caprylate | 5-10% |
| Modified Corn Starch (Dry-Flo ® AF) | 1.5% |
| Water qs | 100 |

Dosage:

Objective 1: 200 mg twice a day (400 mg/day) for a minimum of 4 weeks before surgery to 12 weeks post surgery of TCT or vehicle only (placebo) capsules.

Objective 2: All patients will also apply a dime sized amount per every 10 cm of wound length of TCT cream (20% TCT) or placebo cream to the surgical site. (100 mg of cream per 10 cm of incision)

Recently, it has been suggested that the safe dose of various tocotrienols for human consumption is 200-1000 mg/day. To date, there have been no related adverse affects in the inventors' current IRB protocol (200500034). In this protocol, patients are being supplemented 200 mg TCT twice a day for a minimum of 4 weeks prior to surgery. Based on results from this current protocol, a dosage of 400 mg per day is sufficient to reach the skin.

The subjects and researchers will be blinded as to which patients receive oral TCT and which receive placebo. Subjects and researchers will also be blinded against knowing which side of the participant's body receives topical placebo treatment and topical TCT treatment. The decoding information will be held by The Center of Biostatistics at The Ohio State University and they will also decode the final data.

Patient Eligibility Criteria

Patient Selection: Patients who are scheduled (in a minimum of 4 weeks) for surgical procedures at The Division of Plastic Surgery at the Ohio State University Medical Center involving elective body contouring will be considered for the study. Patients will enter the study a minimum of 4 weeks prior to surgery.

Inclusion Criteria:

To ensure higher enrollment the inventors are not controlling for age of subjects as long as the subjects are 18 years of age or older.

Other inclusion criteria includes: non-smoker, no current medications that alter liver metabolism, e.g Phenobarbital, HmG co-A inhibitors, non-pregnant or non-breastfeeding, no current use of dietary supplements containing vitamin-E not actively abusing drugs or alcohol.

Exclusion criteria are: under 18 years of age, prisoners, current smoker, pregnant or breastfeeding, HIV diagnosis, viral hepatitis diagnosis, immunosuppression therapy, actively abusing drugs or alcohol, current use of dietary supplements containing vitamin-E.

Medical History: The inventors plan to obtain the following medical history from the surgeon or medical doctor: age, race and gender; surgical procedure being performed; a current list of medications; a current list of dietary supplements; any past medical history, genetic diseases use of alcohol.

Treatment Plan

Patient Consenting: Participants will be identified by their plastic surgeon. If the plastic surgeon decides that a patient is eligible to participate in the study (based on the study's inclusion and exclusion criteria), the physician will initiate the consent process by briefly explaining the study and giving the patient an advertisement containing the research nurse or approved personnel's contact information. If interested in participating in the study, the patient can contact the research nurse or approved personnel. After discussing the study with the patient on the telephone, if the patient remains interested in participating, the research nurse or approved personnel will mail the consent and HIPAA forms to the patient's home. After reading the consent form and considering the study, if the patient decides to enroll, an appointment can be scheduled with the research nurse or approved personnel.

Treatment Chronology: Bilateral Site Surgery Patients

1. At the initial appointment with the research nurse or approved personnel, the patient will return/sign the consent and HIPAA forms. A baseline blood draw (20 ml) to measure compliance will occur. Participants will also be given a 4 week supply of oral supplementation (tocotrienol or placebo) as 200 mg×2 per day. Following the initial appointment, until a surgery date is established, a 4 week supply of oral supplementation will be mailed to the participant every 4 weeks. In order to measure compliance, the participant will be instructed to return the empty blister packs to the research nurse or approved personnel in a postage-paid envelope upon receiving a shipment.

Once a Surgery Date is Established:

Four Weeks Prior to Surgery

2. Participants will be given a 4 week supply of oral supplementation (tocotrienol or placebo) as 200 mg×2 per day. Blood (20 ml) will also be drawn to measure compliance (this will be a baseline blood draw if the subject has not started supplementation).

The Day of Surgery:

3. Participants will be given another 4 week supply of oral supplementation (tocotrienol or placebo) as 200 mg×2 per day. Blood (20 ml) will be drawn to measure compliance. Participants will be given tocotrienol cream and placebo cream. A tissue sample will also be collected from the excised surgical specimen.

One Week Post Surgery:

4. Participants will return to the Ohio State Plastic Surgery office. Three independent and blinded medical personnel will assess the participant's surgical site according to the Vancouver Scar Assessment Scale. A photograph of the surgical site will be taken by the research nurse or approved personnel. The photograph will be used for record and/or publication. Blood (20 ml) will be drawn to measure compliance.

Four Weeks Post Surgery:

5. Participants will return to the Ohio State Plastic Surgery office. Three independent and blinded medical personnel will assess the participant's scar and healing process according to the Vancouver Scar Assessment Scale. A photograph of the surgical site will be taken by the research nurse or approved personnel. The photograph will be used for record and/or publication. Blood (20 ml) will be drawn to measure compliance. Participants will be given another 4 week supply of oral supplementation (tocotrienol or placebo) as 200 mg×2 per day. Participants will also be given another container of tocotrienol and placebo cream.

Eight Weeks Post Surgery:

6. Participants will return to the Ohio State Plastic Surgery office. Three independent and blinded medical personnel will assess the participant's scar and healing process according to the Vancouver Scar Assessment Scale. A photograph of the surgical site will be taken by the research nurse or approved personnel. The photograph will be used for record and/or publication. Blood (20 ml) will be drawn to measure compliance. Participants will be given another 4 week supply of oral supplementation (tocotrienol or placebo) as 200 mg×2 per day. Participants will also be given another container of tocotrienol and placebo cream.

Twelve Weeks Post Surgery:

7. Participants will return to the Ohio State Plastic Surgery office for a final visit. Three independent and blinded medical personnel will assess the participant's scar and healing process according to the Vancouver Scar Assessment Scale. A photograph of the surgical site will also be taken by the research nurse or approved personnel. The photograph will be used for record and/or publication.

Single Site Surgery Patients

1. At the initial appointment with the research nurse or approved personnel, the patient will return/sign the consent and HIPAA forms. A baseline blood draw (20 ml) to measure compliance will occur. Participants will also be given a 4 week supply of oral supplementation (tocotrienol or placebo) as 200 mg×2 per day. Following the initial appointment, until a surgery date is established, a 4 week supply of oral supplementation will be mailed to the participant every 4 weeks. In order to measure compliance, the participant will be instructed to return the empty blister packs to the research nurse or approved personnel in a postage-paid envelope upon receiving a shipment.

Once a Surgery Date is Established:

Four Weeks Prior to Surgery:

2. Participants will be given a 4 week supply of oral supplementation (tocotrienol or placebo) as 200 mg×2 per day. Blood (20 ml) will also be drawn to measure compliance (this will be a baseline blood draw if the subject has not started supplementation).

The Day of Surgery:

3. Participants will be given another 4 week supply of oral supplementation (tocotrienol or placebo) as 200 mg×2 per day. Blood (20 ml) will be drawn to measure compliance. Participants will be given tocotrienol cream or placebo cream. A tissue sample will also be collected from the excised surgical specimen.

One Week Post Surgery:

4. Participants will return to the Ohio State Plastic Surgery office. Three independent and blinded medical personnel will assess the participant's surgical site according to the Vancouver Scar Assessment Scale. A photograph of the surgical site will be taken by the research nurse or approved personnel. The photograph will be used for record and/or publication. Blood (20 ml) will be drawn to measure compliance.

Four Weeks Post Surgery:

5. Participants will return to the Ohio State Plastic Surgery office. Three independent and blinded medical personnel will assess the participant's scar and healing process according to the Vancouver Scar Assessment Scale. A photograph of the surgical site will be taken by the research nurse or approved personnel. The photograph will be used for record and/or publication. Blood (20 ml) will be drawn to measure compliance. Participants will be given another 4 week supply of oral supplementation (tocotrienol or placebo) as 200 mg×2 per day. Participants will also be given another container of tocotrienol or placebo cream.

Eight Weeks Post Surgery:

6. Participants will return to the Ohio State Plastic Surgery office. Three independent and blinded medical personnel will assess the participant's scar and healing process according to the Vancouver Scar Assessment Scale. A photograph of the surgical site will be taken by the research nurse or approved personnel. The photograph will be used for record and/or publication. Blood (20 ml) will be drawn to measure compliance. Participants will be given another 4 week supply of oral supplementation (tocotrienol or placebo) as 200 mg×2 per day. Participants will also be given another container of tocotrienol or placebo cream.

Twelve Weeks Post Surgery:

7. Participants will return to the Ohio State Plastic Surgery office for a final visit. Three independent and blinded medical personnel will assess the participant's scar and healing process according to the Vancouver Scar Assessment Scale. A photograph of the surgical site will also be taken by the research nurse or approved personnel. The photograph will be used for record and/or publication.

Subjects will be required to self administer two 100 mg capsules twice a day approximately 12 hours apart. They will also be required to topically apply a dime sized amount of cream per 10 cm of wound length to the surgical incision site. The creams will be applied once daily (in the morning) beginning the day after surgery. In order to assess compliance, subjects will be required to bring their empty blister packs and cream tubes with them during every clinic visit, if applicable. The research nurse or approved personnel will count any remaining capsules that are present and weigh the tubes. Patients will provide a blood sample of four teaspoons (20 ml) during every clinic visit, aside from the last. A maximum of 6 blood draws will be taken and a minimum of 5. The research nurse will be drawing blood from the patient. The nurse will also demonstrate how and how much cream to apply to each surgical site. The patients will be given a randomized diagram, similar to the one shown above, explaining where to apply each labeled, color-coded cream. On the day of surgery, a tissue sample will also be collected from the excised surgical specimen. Medical personnel will assess the actual scars and surgical sites. Photographs will be taken for record and for possible publication. No personal identifying features will be included in the photographs.

Rationale for Vancouver Scar Assessment:

Healing scars are commonly characterized by definitions concerning the depth of elevated tissue, the color, softness, shape, and orientation. Evolution of the proliferative process and histo-pathological differences are also used to differentiate hypertrophic scar, a process generally limited in time, from keloid, which involves a permanently evolving productivity of cell, covering the initial edges and extending beyond the original scar boundary into the surrounding skin.

For surgical scar assessment, the Vancouver Scar Scale is associated with acceptable internal consistency and observer reliability [49]. Participants' scars will be assessed by three independent medical personnel according to the scale listed below. The Vancouver Scar Scale is a quantitative assessment for scar formation. Normal skin has a Vancouver Scar Scale score sum of zero.

Adverse Events:

To date, there have been no related adverse affects in the inventors' current IRB protocol (2005C0034). In this protocol, patients are being supplemented 200 mg TCT twice a day for a minimum of 4 weeks prior to surgery. The maximum supplementation has been for over a year (currently on-going supplementation).

Vitamin E is a nutrient and the dosage used is less than half of the UL (upper limit; 1000 mg/day) assigned by the Food and Nutrition Board of the Institute of Medicine. Thus, complications are not expected. If an adverse event occurs, the participant will discontinue the use of the Vitamin E and will also be scheduled to see their plastic surgeon. Any adverse events will be reported as protocol.

Study Outcomes

Scar formation will be analyzed using the Vancouver Scar Scale. The data will be analyzed by The Center for Biostistics at The Ohio State University. The average Vancouver Scar Scale score will be used for each patient at each time point. The first endpoint of this study will occur after half of the patients have been enrolled. The Center of Biostastics will analyze the data at this point. Pictures from the surgical area may be used in publication, but will be deidentified if used. The study will provide first evidence indicating whether tocotrienol will have an effect on preventing or reducing scar formation.

Statistical Considerations

Sample Size:

The primary objective of this randomized double-blind study is to determine if oral and topical administration of tocotrienol (TCT) improves scarring after surgery using the Vancouver Scar Scale (VSS). The VSS ranges from 0 to 13 where 0 is the least amount of scarring and 13 is the most amount of scarring. Surgical scars will be scored on day 1 post surgery, 4, 8, and 12 weeks post surgery. Subjects will be randomized to one of four groups defined by: I) oral placebo/topical placebo, II) oral placebo/topical TCT, III) oral TCT/topical placebo, or IV) oral TCT/topical TCT if unilateral surgery. If subjects are scheduled for bilateral surgery, then they will be randomized to either oral placebo or oral TCT where each subject receives topical TCT randomized to their left or right side and topical placebo applied to the other side. Thus in bilateral surgery, subjects will receive both the treatment and control for the topical administration. Five specific hypotheses will be tested. The first compares VSS scores between oral TCT and oral placebo. The second compares topical TCT and topical placebo. The third compares oral and topical TCT to oral and topical placebo. The fourth compares oral TCT and topical placebo to oral and topical placebo and the fifth compares topical TCT and oral placebo to oral and topical placebo. The overall significance level of 0.05 was divided by 5 as there are five primary hypotheses to be tested thus controlling for type I error. Thirty-seven wound sites (37) per group will have an 80% power to detect a difference of 1.4 units on the VSS. This estimate is based on a two-sided t-test at a 0.01 significance level that has a common standard deviation of 1.7 VSS units [49]. The VSS means and common standard deviation are based on Conologue and Norwood's [50] work to treat surgical scars. VSS scoring at week 12 post surgery will be the primary outcome in the five hypothesis tests. Assuming that 10% of the subjects are lost to follow up, 42 wound sites per group will be needed to insure the study is powered correctly giving a total sample size of 168 wound sites. The distribution of single surgical sites and bilateral surgical sites is unknown at this point. If all of the subjects that enter into this study were single site subjects, then the number of subjects and wound sites would be the same and 168 subjects would be needed for the study. On the other hand if all of the subjects required bilateral surgery, then only 84 subjects would be needed to obtain 168 wound sites. The actual number of subjects needed will be between 84 and 168, however, there will be 168 wound sites independent to the distribution of surgery types.

Interim Analysis:

One interim analysis will be run half way through the trial after approximately 84 subjects have been randomized using the alpha spending method of DeMets and Lan[51] with O'Brien-Fleming [52] boundaries for the two analyses (interim and final analysis). The trial will be stopped if the p-value for the difference in the VSS scores between oral and topical TCT compared to oral and topical placebo is less than 0.0054.

Statistical Analysis:

Descriptive statistics will be used to characterize patient demographics and clinical outcomes. The primary analysis will use a random intercept mixed model where VSS on week 12 post surgery will be regressed on the four treatment groups and adjusted for confounders such as patient demographics and scar location. The p-values from the five tested hypotheses will be adjusted to conserve the overall type I error rate at 0.0492. Secondary analyses will test healing rates between the four treatment groups using a random coefficient mixed model that uses VSS at all time points. VSS scores will be based on the results of three independent observers. A rater term will also be included in the above models. Interrater agreement will be checked using the kappa statistic. VSS scores will be tested for normality and equal variance both of which are necessary for the mix model. The VSS may be transformed in order to meet these assumptions. All analyses will be run using Stata 9.2 or higher, Stata Corporation, College Station, Tex.

APPENDIX

Vancouver Scar Scale
Vascularity
0 pt.—normal color that closely resembles the color over the rest of the body.
1 pt.—pink. This color, usually observed during a transient period of time in most of the normal maturation processes, becomes a warning signal of pathological scar when it remains present after the second month of evolution.
2 pt.—red. A red aspect is linked to a scar hypervascularization. This color becomes obvious 4 to 8 weeks after complete healing and is a good sign of pathologic evolution. Usually, a red scar is combined with a progressive elevation, defining a scar hypertrophy.
3 pt.—purple. A purple scar is observed in highly vascularized scars, like burn scars or at the initial stage of a keloid process.
Pigmentation
0 pt.—normal skin
1 pt.—hypopigmentation
2 pt.—hyperpigmentation Pliability
0 pt.—normal,
1 pt.—supple: flexible with minimal resistance,
2 pt.—yielding: giving way to pressure,
3 pt.—firm: inflexible, not easily moved, resistant to manual pressure,
4 pt—banding: producing striations which blanch on stretching but with no limit to the range of motion,
5 pt.—contracture of any type of scar limiting the range of motion.
Height
0 pt.—normal
1 pt.—height (h)<2 mm
2 pt.—2 mm<h<5 mm
3 pt.—h>5 mm
Total possible score=13

All publications, including patents and non-patent literature, referred to in this specification are expressly incorporated by reference herein. Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. A method to improve skin scar or burn outcome in a subject with a skin scar or burn pathology, comprising:
    a) administering daily for at least 4 weeks to a subject with skin scar or burn pathology a topical formulation comprising 30% of a vitamin E formulation, the vitamin E formulation comprising a minimum of 15% tocotrienols selected from the group consisting of: alpha-tocotrienol; beta-tocotrienol; gamma-tocotrienol; and delta-tocotrienol; wherein the topical formulation further comprises

| | |
|---|---|
| methyl paraben | 0.1%, |
| propyl paraben | 0.01%, |
| carbomer | 0.3%, |
| glycerin | 4.0%, |
| triethanolamine | 0.6%, |
| polyoxyl 40 castor oil | 1-5%, |
| emulsifying wax | 5%, |
| cetyl alcohol | 1.5%, |
| stearic acid | 1.5%, |
| propylene glycol caprylate | 5-10%, |
| modified corn starch | 1.5%, and |
| water qs | 100; | and
    b) improving skin scar or burn outcome in the subject.

2. The method of claim 1, wherein the subject is intolerant of standard therapeutic measures.

3. The method of claim 1, further comprising administering an oral tocotrienol composition having approximately 15-30% alpha-tocotrienol, approximately 30-50% gamma-tocotrienol, approximately 2-15% delta tocotrienol, and approximately 20-30% alpha tocopherol, by weight of those four ingredients.

4. The method of claim 3, wherein the oral tocotrienol composition comprises approximately 23% alpha-tocotrienol, approximately 41% gamma-tocotrienol, approximately 9% delta tocotrienol, and approximately 25% alpha tocopherol, by weight of those four ingredients.

5. The method of claim 3, wherein the oral tocotrienol composition is free of tocopherol.

6. The method of claim 1, wherein the tocotrienols are derived from at least one plant selected from the group consisting of: wheat; rice; barley; and palm.

7. The method of claim 1, wherein the tocotrienols are derived from palm oil.

8. The method of claim 1, wherein the scar is a result of a cause selected from the group consisting of: scrape; cut; laceration; surgery; abrasion; and acne.

9. The method of claim 1, wherein the scar type is selected from the group consisting of: hypertrophic; keloid; atrophic; and stretch.

10. The method of claim 3, wherein oral administration is daily for 4 weeks, after meals.

11. The method of claim 1, wherein scar and burn outcome is measured by a means selected from the group consisting of: Vancouver scar assessment; transepidermal water loss (TEWL); and surface electrical capacitance (SEC).

12. The method of claim 1, wherein the topical administration is a dosage of 100 mg per 10 cm of skin scar or burn tissue.

13. The method of claim 1, wherein the topical formulation is topically administered daily for at least 12 weeks after a surgery producing a skin scar.

14. The method of claim 3, wherein the oral tocotrienol composition is orally administered daily for at least 4 weeks before a surgery producing a skin scar.

15. The method of claim 3, wherein the oral tocotrienol composition is orally administered daily for at least 12 weeks after a surgery producing a skin scar.

* * * * *